(12) United States Patent
Cho et al.

(10) Patent No.: US 10,266,504 B2
(45) Date of Patent: Apr. 23, 2019

(54) POLYBENZOXAZINE PRECURSOR AND METHOD FOR PREPARING SAME

(71) Applicant: KOLON INDUSTRIES, INC., Gwacheon-si, Gyeonggi-do (KR)

(72) Inventors: Hee Jin Cho, Yongin-si (KR); Do Kyung Sung, Yongin-si (KR); Ki Hyun Park, Yongin-si (KR); Sang Hun Park, Yongin-si (KR); Hyun Soo Kagn, Yongin-si (KR)

(73) Assignee: KOLON INDUSTRIES, INC., Seoul (KR)

( * ) Notice: Subject to any disclaimer, the term of this patent is extended or adjusted under 35 U.S.C. 154(b) by 0 days.

(21) Appl. No.: 15/322,946

(22) PCT Filed: Jun. 30, 2015

(86) PCT No.: PCT/KR2015/006715
§ 371 (c)(1),
(2) Date: Dec. 29, 2016

(87) PCT Pub. No.: WO2016/003167
PCT Pub. Date: Jan. 7, 2016

(65) Prior Publication Data
US 2017/0137391 A1    May 18, 2017

(30) Foreign Application Priority Data

Jun. 30, 2014 (KR) .................. 10-2014-0081402
Jul. 24, 2014 (KR) .................. 10-2014-0094203
Dec. 5, 2014 (KR) .................. 10-2014-0174117
Jun. 30, 2015 (KR) .................. 10-2015-0092996

(51) Int. Cl.
*C08G 61/00* (2006.01)
*C07D 265/14* (2006.01)
*C08G 61/12* (2006.01)
*C07D 265/12* (2006.01)
*C07D 413/10* (2006.01)

(52) U.S. Cl.
CPC ......... *C07D 265/14* (2013.01); *C08G 61/122* (2013.01); *C08G 2261/135* (2013.01); *C08G 2261/1644* (2013.01); *C08G 2261/60* (2013.01); *C08G 2261/65* (2013.01); *C08G 2261/76* (2013.01)

(58) Field of Classification Search
CPC ...................................................... C08G 61/00
USPC ........................................................ 528/210
See application file for complete search history.

(56) References Cited

U.S. PATENT DOCUMENTS 5,543,516 A    8/1996    Ishida

FOREIGN PATENT DOCUMENTS

| | | |
|---|---|---|
| JP | 2003-064155 A | 3/2003 |
| JP | 2003-286320 A | 10/2003 |
| KR | 10-0818254 B | 3/2008 |
| KR | 10-2012-0058566 A | 6/2012 |
| KR | 10-2013-0131870 A | 12/2013 |
| KR | 10-2014-0007856 A | 1/2014 |
| KR | 10-2014-0067006 A | 6/2014 |

OTHER PUBLICATIONS

International Searching Authority, International Search Report for application No. PCT/KR2015/006715 dated Aug. 25, 2015.
Korean Intellectual Property Office, Office Action for Korean application No. 10-2015-0092996 dated Nov. 14, 2016.

*Primary Examiner* — Duc Truong
(74) *Attorney, Agent, or Firm* — Sughrue Mion, PLLC (57) ABSTRACT

Disclosed is a polybenzoxazime precursor and a method of preparing the same. The polybenzoxazime precursor is used to prepare a hardened material having improved thermal characteristics, having high thermal and flame-retardant characteristics while maintaining its excellent electrical characteristics, or having high thermal and electrical characteristics, thus being available for use in a copper clad laminate, a semiconductor encapsulate, a printed circuit board, an adhesive, a paint, and a mold.

19 Claims, 6 Drawing Sheets

POLYBENZOXAZINE PRECURSOR AND METHOD FOR PREPARING SAME

CROSS REFERENCE TO RELATED APPLICATIONS

This application is a National Stage of International Application No. PCT/KR2015/006715, filed on Jun. 30, 2015, which claims priority from Korean Patent Application Nos. 10-2014-0081402 filed on Jun. 30, 2014, 10-2014-0094203 filed on Jul. 24, 2014, 10-2014-0174117 filed on Dec. 5, 2014, and 10-2015-0092996 filed Jun. 30, 2015, the contents of all of which are incorporated herein by reference in their entirety.

TECHNICAL FIELD

The present invention relates to a polybenzoxazime precursor and a method of preparing the same.

BACKGROUND ART

Thermosetting resins such as phenol resins, melamine resins, epoxy resins, unsaturated polyester resins, and bismaleimide resins are based on thermosetting properties and are excellent in water resistance, chemical resistance, heat resistance, mechanical strength, and reliability. Accordingly, thermosetting resins have been widely used in various industrial fields.

However, the phenol resins and the melamine resins have drawbacks in that volatile byproducts are generated during hardening, the epoxy resins and the unsaturated polyester resins have a drawback of poor flame retardancy, and the bismaleimide resins have a drawback of very high costs.

In order to solve the drawbacks, there has been studied polybenzoxazime obtained by performing a ring-opening polymerization reaction on a benzoxazine ring, which leads to thermosetting, without the generation of volatile matter, which is considered to be a problem.

To obtain a thermosetting resin having a benzoxazine ring in the molecular structure thereof, an oxazine ring is opened by heating and polymerization is performed without the generation of byproducts. Accordingly, the thermosetting resin having the benzoxazine ring is receiving attention as a thermosetting resin used in an encapsulant, an impregnating agent, a laminate, an adhesive, a paint, a coating material, a friction material, FRP, and a molding material. The benzoxazine ring has a complex structure including benzene and oxazine rings.

Polybenzoxazines are hardened polymers having a high glass transition temperature (Tg), low permittivity, high tension, a low coefficient of thermal expansion, excellent elasticity, and low hygroscopicity, thus maintaining a balance between mechanical, electrical, and chemical properties.

Techniques for further enhancing the properties of polybenzoxazines have been continuously developed. For example, Korean Laid-Open Patent Application No. 10-2012-0058566 relates to a "polybenzoxazime composition", and discloses a method of preparing polybenzoxazime having favorable thermal stability, the method including heating a curable composition including a benzoxazine compound and a pentafluoroantimony acid catalyst at a sufficient temperature for a sufficient time to thus achieve polymerization.

Further, Korean Patent No. 10-0818254 relates to "a polybenzoxazime-based compound, an electrolyte membrane including the same, and a fuel cell using the same", and discloses a novel polybenzoxazime-based compound having improved acid trapping performance, mechanical and chemical stability, and ability to retain phosphoric acid at high temperatures, an electrolyte membrane using the same, and a method of preparing the same.

With recently increased interest in the environment at home and abroad, environmental problems have started to become an issue in the electronic material industry. Due to the RoHS directive, which limits the use of hazardous substances in the European Union and developed countries, eco-friendly lead-free PCB technologies are increasingly adopted in the domestic electronic circuit board industry. As lead is not used during an eco-friendly lead-free process, the working temperature is increased during the process. Accordingly, materials that can withstand high temperatures and equipment suitable for the materials must be developed.

Epoxy resins are frequently used as coatings, insulation, building materials, and adhesives, where they help ensure easy handling, high stability, and excellent mechanical and chemical properties. An epoxy resin composition needs to have heat resistance and flame retardancy for the purpose of lead-free application. Particularly, in the case of a CCLS (copper clad laminate sheet) epoxy resin composition, the V-0 certification of the UL-94 standard is essentially required. In the related art, a halogenated resin, such as a brominated epoxy resin, and antimony oxide are used to impart the flame retardancy.

Current halogen-based flame retardants generate gas during injection and dioxin during incineration, thus negatively affecting the environment. The electric, electronic, and semiconductor industries are major industries in Korea, and account for a large portion of industry in Korea. Particularly, there is a great demand for a semiconductor-industry technique regarding the flame retardancy of the encapsulant and the adhesive for semiconductors, and there is growing interest in the development of a raw material for replacing the flame retardant, which is harmful to the environment.

As an alternative thereof, the use of polybenzoxazime, which is a phenol-based hardening agent, has been emphasized. As described above, polybenzoxazime is a thermosetting polymer obtained by polymerizing a benzoxazine-based monomer while a ring is opened in a molecule of the monomer by heat. Polybenzoxazime can be self-hardened without byproducts and does not generate volatile materials and is not changed in volume while hardening, thus ensuring excellent dimensional stability. Further, polybenzoxazime is a highly heat-resistant polymer having a high glass transition temperature and decomposition of less than 1% at thermal decomposition temperatures up to 350° C. Further, since polybenzoxazime is a nitrogen-containing compound suitable for use in halogen-free products, it serves as a flame retardant.

However, conventionally developed polybenzoxazime fails to exhibit a sufficient flame-retardant effect, and accordingly, additives such as bromine, phosphorus, or chlorine compounds are added to the polybenzoxazime-containing flame retardant. These additives are not dissolved in a solvent and thus result in a hardened resin that may cause problems during a processing process and that has poor oxidative stability at high temperatures and poor physical properties.

Therefore, there is a need to prepare highly flame-retardant polybenzoxazime that may be used in high-temperature environments without revealing the above-described drawbacks.

Meanwhile, a copper clad laminate (CCL) is a laminate with a thin copper foil on an insulating material. In accordance with the recent high performance and high integration of smart devices, a copper clad laminate used in a printed circuit board (PCB) is required to have excellent heat resistance and low permittivity. A resin is used as the base material of the copper clad laminate, and serves as an insulator in the printed circuit board. Permittivity must be low in order to form an excellent insulator. "Permittivity" refers to the degree of polarization of molecules in a nonconductor relative to an external electrical signal. The smaller the permittivity, the better the insulating performance. As the permittivity of the insulator is reduced during the operation of the printed circuit board, the processing speed of the signal is increased and a transmission loss is reduced.

As an alternative to satisfy the requirements for heat resistance and low permittivity of the above-described copper clad laminate, the use of polybenzoxazime, which is a phenol-based hardening agent, has been emphasized. As described above, polybenzoxazime is a thermosetting polymer obtained by polymerizing a benzoxazine-based monomer while a ring is opened in a molecule of the monomer by heat. Polybenzoxazime can be self-hardened without byproducts, does not generate volatile materials, and is not changed in terms of volume during hardening, thus ensuring excellent dimensional stability.

(Patent Document 1) Korean Laid-Open Patent Application No. 10-2012-0058566

(Patent Document 2) Korean Patent No. 10-0818254

DISCLOSURE

Technical Problem

Accordingly, the present invention has been made keeping in mind the above problems occurring in the related art, and an object of the present invention is to provide a polybenzoxazime precursor which is used to prepare a hardened material the thermal characteristics of which are improved compared to a conventional polybenzoxazime precursor.

Another object of the present invention is to provide a polybenzoxazime precursor which is used to prepare a hardened material that has greatly improved thermal and flame-retardant characteristics while maintaining its electrical characteristics, compared to a conventional polybenzoxazime precursor.

A further object of the present invention is to provide a polybenzoxazime precursor which is used to prepare a hardened material, having greatly improved thermal and electrical characteristics, compared to a conventional polybenzoxazime precursor.

Yet another object of the present invention is to provide a method of preparing the aforementioned polybenzoxazime precursor.

Still another object of the present invention is to provide a hardened material of the aforementioned polybenzoxazime precursor.

Technical Solution

In order to accomplish the above objects, the present invention provides a polybenzoxazime precursor including a benzoxazine compound represented by the following Chemical Formula 1, wherein a content of the benzoxazine compound represented by Chemical Formula 1 is 20 to 100% when n is 0.

[Chemical Formula 1]

In Chemical Formula 1, n is an integer of 0 to 2, and $R_1$ is

The polybenzoxazime precursor according to an embodiment may include a self-hardened material obtained by opening an oxazine ring of the benzoxazine compound represented by Chemical Formula 1 to perform polymerization.

In the embodiment, the self-hardened material of the benzoxazine compound may include a compound represented by the following Chemical Formula 2.

[Chemical Formula 2]

In Chemical Formula 2, R is $R_1$ is n is an integer of 0 to 2, and n2 is an integer of 1 to 5.

The polybenzoxazime precursor according to the embodiment may have a weight average molecular weight of 500 to 5000 g/mol.

In order to accomplish the above objects, the present invention also provides a method of preparing a polybenzoxazime precursor, comprising the steps of (1) obtaining a phenol novolak resin by reacting a phenol-based compound with an aldehyde compound in the presence of an acid catalyst, and (2) reacting the obtained phenol novolak resin with an aldehyde compound and an amine compound including allylamine or aniline.

In the embodiment, the phenol novolak resin is represented by Chemical Formula 3, wherein a content of the phenol novolak resin represented by Chemical Formula 3 that n is 0 is 65% or more.

[Chemical Formula 3]

In Chemical Formula 3, n is an integer of 0 to 2.

In the embodiment, the aldehyde compound may be used in a content of 0.05 to 0.3 mol based on 1 mol of the phenol-based compound in the step (1), and the amine compound may be used in a content of 1 to 3 mol and the aldehyde compound may be used in a content of 1 to 5 mol based on 1 mol of the phenol novolak resin in the step (2).

In order to accomplish the above objects, the present invention also provides a hardened material of the polybenzoxazime precursor of the above-described embodiment.

In the embodiment, the hardened material may include a self-hardened material of the polybenzoxazime precursor including a benzoxazine compound represented by Chemical Formula 1 where $R_1$ is and may have a glass transition temperature of 190° C. or higher.

In the embodiment, the hardened material may include a self-hardened material of the polybenzoxazime precursor including a benzoxazine compound represented by Chemical Formula 1 where $R_1$ is and may have a glass transition temperature of 250° C. or higher.

Advantageous Effects

A polybenzoxazime precursor according to the present invention may be used to provide a hardened material the thermal characteristics of which are improved compared to a conventional polybenzoxazime precursor.

Particularly, according to an embodiment, the hardened material may have high thermal and flame-retardant characteristics while maintaining its electrical characteristics.

According to another embodiment, the hardened material may have high thermal and electrical characteristics, thus being available for use in a copper clad laminate, a semiconductor encapsulant, a printed circuit board, an adhesive, a paint, and a mold.

BEST MODE

Unless defined otherwise, all the technical and scientific terms used in this specification have the same meanings as would be generally understood by those skilled in the related art to which the present invention pertains. In general, the nomenclature used herein is well known and commonly used in the art.

In the specification, when any portion "includes" any component, this means that the portion does not exclude other components, but may further include other components unless otherwise stated.

The terms "about", "substantially", etc., as used herein, are intended to be taken to mean an approximation to a numerical value when presenting the preparation and material tolerances inherent in the meanings mentioned, and also to prevent disclosure content mentioning accurate or absolute numerical values from being misconstrued, thereby helping the understanding of the present invention.

The present invention provides a polybenzoxazime precursor including a benzoxazine compound represented by the following Chemical Formula 1, wherein a content of the benzoxazine compound represented by Chemical Formula 1 is 20 to 100% when n is 0.

[Chemical Formula 1]

In Chemical Formula 1, n is an integer of 0 to 2, $R_1$ is

.

Throughout the specification, the term "polybenzoxazime precursor" means a compound or a compound group that serves as a precursor for forming a thermosetting resin which is obtained using a ring-opening reaction of an oxazine ring and which is called polybenzoxazime. The polybenzoxazime precursor is defined to include only benzoxazine-based monomers, to include oligomers including the monomers and a repeating-unit structure on a main chain thereof, or to include a combination including a portion of self-hardened materials obtained by polymerizing the monomers or the oligomers while opening the oxazine rings thereof.

Preferably, in order to improve electrical, thermal, and flame-retardant characteristics, a polybenzoxazime precursor according to an embodiment of the present invention may include the compound, which is represented by Chemical Formula 1, so that the content of the compound is at least 20% based on the total composition when n is 0.

The percentage (%) is based on the peak area ratio of a gel permeation chromatography (GPC) (Waters: Waters707), and specifically means the peak area ratio between monomer and polymer components when the precursor includes the polymer such as the self-hardened material throughout the present specification.

The polybenzoxazime precursor according to the embodiment of the present invention may include also the compound of Chemical Formula 1 where n is 1 to 2, except the compound of Chemical Formula 1 where n is 0, and may include the self-hardened material as described above.

In Chemical Formula 1, the self-hardened material is formed by polymerizing benzoxazine-based monomers or oligomers while the oxazine ring is opened.

The self-hardened material, which is included in the polybenzoxazime precursor satisfying the above-described condition, may include a compound represented by the following Chemical Formula 2.

[Chemical Formula 2]

In Chemical Formula 2, R is

,

$R_1$ is

, n is an integer of 0 to 2, and n2 is an integer of 1 to 5.

In Chemical Formula 1, the compound of $R_1$, which is a functional group resulting from an amine compound, and the self-hardened material thereof may correspond to Chemical Formulas 4 and 5 and Chemical Formulas 6 and 7, respectively.

[Chemical Formula 4]

In Chemical Formula 4, n is an integer of 0 to 2.

[Chemical Formula 5]

R is n is an integer of 0 to 2, and n2 is an integer of 1 to 5.

[Chemical Formula 6]

In Chemical Formula 6, n is an integer of 0 to 2.

[Chemical Formula 7]

In Chemical Formula 7, R is n is an integer of 0 to 2, and n2 is an integer of 1 to 5.

The polybenzoxazime precursor may have a weight average molecular weight of preferably 500 to 5000 g/mol and more preferably 900 to 1800 g/mol in order to prevent delaying of hardening or crystallization during hardening, a reduction in workability due to the increased viscosity of the precursor or gelation of the precursor, and a reduction in compatibility with other resins.

The weight average molecular weight may be defined by the converted value of the equivalent of polystyrene, determined using gel permeation chromatography (GPC).

The polybenzoxazime precursor according to the present invention may serve to provide a hardened material having thermal characteristics that are improved compared to those of a conventional polybenzoxazime precursor.

Particularly, in Chemical Formula 1, when the polybenzoxazime precursor includes the compound where $R_1$ is (Chemical Formula 4)

thermal and flame-retardant characteristics may be greatly improved while excellent electrical characteristics are maintained.

Meanwhile, in Chemical Formula 1, when the polybenzoxazime precursor includes the compound where $R_1$ is

(Chemical Formula 6)

the polybenzoxazime precursor may serve to provide a hardened material having greatly improved thermal and electrical characteristics.

The phenol novolak resin represented by the following Chemical Formula 3 may be used as a raw material to prepare the polybenzoxazime precursor of the present invention.

[Chemical Formula 3]

In Chemical Formula 3, n is an integer of 0 to 2.

Specifically, the phenol novolak resin, including 65% or more of the compound of Chemical Formula 3 where n is 0, may be used as the raw material to prepare the polybenzoxazime precursor.

More specifically, the polybenzoxazime precursor may be prepared using a method which includes the steps of (1) obtaining a phenol novolak resin by reacting a phenol-based compound with an aldehyde compound in the presence of an acid catalyst, and (2) reacting the obtained phenol novolak resin with an aldehyde compound and an amine compound including allylamine or aniline.

Still more specifically, the phenol-based compound and the aldehyde compound are reacted in the presence of the acid catalyst to obtain the phenol novolak resin including 65% or more (GPC area %) of the compound of Chemical Formula 3 where n is 0. Subsequently, the obtained phenol novolak resin undergoes a condensation reaction with the aldehyde compound and the amine compound in the presence of a solvent, thus preparing the polybenzoxazime precursor containing benzoxazine in a maximum content of aromatics.

As described above, the phenol-based compound and the aldehyde compound are reacted in the presence of the acid catalyst to obtain a phenol novolak resin including 65% or more (GPC area %) of the compound of Chemical Formula 3 where n is 0. When the content of the compound of Chemical Formula 3 where n is 0 is less than 65%, a viscosity may be increased or gelation may occur due to the rapid reactivity and the large molecular weight of the raw material during the preparation of benzoxazine.

Water and the solvent generated during the reaction may be removed using a known method such as distillation.

In the step (1), the aldehyde compound may be added in a content of 0.05 to 0.3 mol, and preferably 0.1 to 0.2 mol, based on 1 mol of the phenol-based compound. When the aldehyde compound is added in a content of less than 0.05 mol based on 1 mol of the phenol-based compound, the yield may be rapidly reduced. When the content is more than 0.3 mol, the synthesized phenol novolak resin may include 65% or less of the component of Chemical Formula 3, where n is 0.

The phenol-based compound may be phenol or cresol.

Further, the aldehyde compound is not particularly limited, but specific examples thereof may include one or more selected from the group consisting of benzaldehyde, anisaldehyde, 4-methylbenzaldehyde, 2-methoxybenzaldehyde, 4-methoxybenzaldehyde, 3,4-methylenedioxybenzaldehyde, 3,4-dimethoxy-benzaldehyde, and 3-isopropoxy-benzaldehyde.

Examples of the acid catalyst used in the step (1) may include one or more selected from the group consisting of para-toluene sulfonic acid, methyl sulfonic acid, boron trifluoride, aluminum chloride, and sulfonic acid.

In the step (2), the amine compound may be added in a content of 1 to 3 mol, and preferably 1.5 to 2.5 mol, based on 1 mol of the phenol novolak resin, and the aldehyde compound may be added in a content of 1 to 5 mol, and preferably 2.5 to 4.5 mol, based on 1 mol of the phenol novolak resin.

In the case where the amine is aniline, when amine is added in a content of less than 1 mol based on 1 mol of the phenol novolak resin, since a ring closure reaction does not occur, benzoxazine may be insufficiently reacted (a benzoxazine ring may be formed in an insufficient amount). When the content is more than 3 mol, since mind bridges are formed in an excessive amount, heat-resistant and flame-retardant characteristics may be reduced, gelation may occur due to secondary amine in a molecule thereof, or the molecular weight may be increased, thus reducing the compatibility with the resin.

Meanwhile, in the case where the amine is allylamine, when the amine is added in a content of less than 1 mol based on 1 mol of the phenol novolak resin, since a ring closure reaction does not occur, benzoxazine may be insufficiently reacted (a benzoxazine ring may be formed in an insufficient amount). When the content is more than mol, since mind bridges are formed in an excessive amount, heat-resistant and electric characteristics may be reduced, gelation may occur due to the secondary amine in a molecule thereof, or the molecular weight may be increased, thus reducing compatibility with the resin.

Further, when the aldehyde compound is added in a content of less than 1 mol based on 1 mol of the phenol novolak resin, since the reaction with the amine compound insufficiently occurs, the oxazine ring may not be formed and the heat-resistant characteristic may be reduced. When the content is more than 5 mol, an excessive amount of unreacted raw materials may remain in the product.

Examples of the solvent used in the reaction may include aromatic hydrocarbon-based solvents such as toluene, xylene, and trimethylbenzene; halogen-based solvents such as chloroform, dichloroform, and dichloromethane; and ether-based solvents such as THF and dioxane. Preferably, the content of the solvent is 25 to 100 parts by weight based on 100 parts by weight of the phenol novolak resin, the aldehyde compound, and the amine compound, and the content is 50 to 80 parts by weight when aniline is used as the amine.

During the preparation of the polybenzoxazime precursor, when the content of the solvent is very low, the viscosity of the reactant is increased, thus increasing alternating stress and reducing workability. When the content is very high, the cost of solvent removal after the reaction may be uneconomically increased. Further, when the solvent is not appropriately selected and the mixing reaction is not performed as desired, the raw materials do not readily participate in the reaction, thus reducing the yield.

The prepared polybenzoxazime precursor may include 20 to 100% of the component of Chemical Formula 1 where n is 0.

The embodiment of the present invention may provide the hardened material of the polybenzoxazime precursor. The hardened material may have improved thermal characteristics compared to a hardened material derived from a conventional benzoxazine compound.

Particularly, when the hardened material is obtained from a polybenzoxazime precursor including 20% or more of the compound represented by Chemical Formula 4 where n is 0, the hardened material may have high thermal and flame-retardant characteristics while maintaining excellent electrical characteristics, thus being available for use in a copper clad laminate, a semiconductor encapsulant, a printed circuit board, an adhesive, a paint, and a mold.

Meanwhile, when the hardened material is obtained from the polybenzoxazime precursor including 20% or more of the compound represented by Chemical Formula 6 where n is 0, the hardened material may have high thermal and electrical characteristics, thus being available for use in a copper clad laminate, a semiconductor encapsulant, a printed circuit board, an adhesive, a paint, and a mold.

Throughout the specification, the term "hardened material" may not only mean the self-hardened material of the single polybenzoxazime precursor but may also include the hardened material including the polybenzoxazime precursor resin and other resin-based compositions mixed therein.

Mode for Invention

A better understanding of the present invention may be obtained through the following Examples which are set forth to illustrate, but are not to be construed to limit the present invention.

EXAMPLE 1

1-1: Preparation of Polybenzoxazime Precursor 202.97 g of benzaldehyde and 1200.0 g of phenol were added at 40° C., and were reacted under a para-toluene sulfonic acid catalyst, which was an acid catalyst, at 130° C. for 5 hours, thus obtaining a phenol novolak resin containing 75.02% of 4,4-(phenylmethylene)diphenol (GPC area %) and 24.98% of the following compound where n is 1 to 2 (Chemical Formula 3) as the residue.

Figure 1A:
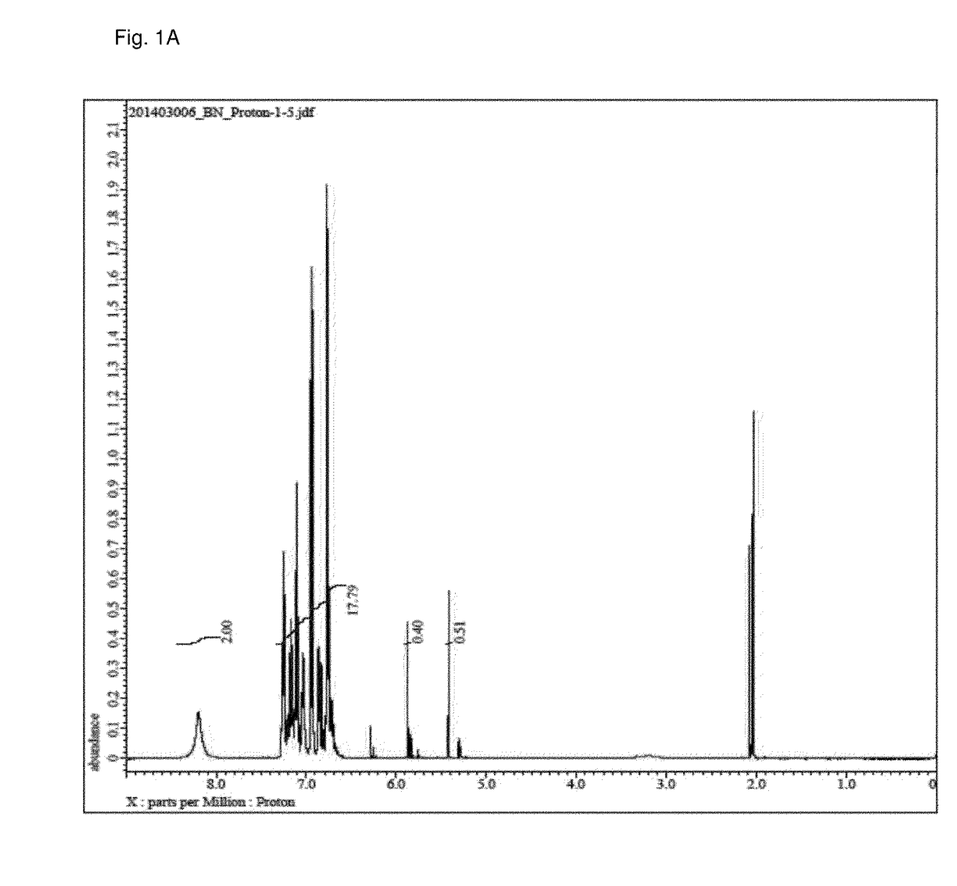
FIG. 1A shows the $^1$H-NMR spectrum of a phenol novolak resin prepared in Example 1 of the present invention.

The structure of the obtained phenol novolak resin was confirmed using a nuclear magnetic resonance analysis method ($^1$H-NMR). The result is shown in FIG. 1A, and a —OH peak is observed around 8.0 ppm.

An Avance 500, manufactured by Bruker Co., Ltd. was used as the NMR equipment during NMR analysis.

[Chemical Formula 3]

Next, 500 g (1.8094 mol) of the synthesized phenol novolak resin and 222.8 g of toluene were added to a 3 L three-neck flask subjected to purging using nitrogen. 168.51 g (1.8094 mol) of aniline and 271.69 g (3.6189 mol) of a formaldehyde aqueous solution (40%) were added thereto. After the completion of addition, the temperature of the reaction solution was increased to 100° C. at a heating rate of 1.3° C./min, and the reaction solution was then agitated for 5 hours. Subsequently, the temperature was increased to 120° C., and a solvent was completely removed under pressure of 10 torr for 60 min, thus preparing 708 g of a polybenzoxazime precursor having a weight average molecular weight of 652 g/mol (the polybenzoxazime precursor included the component represented by Chemical Formula 4 where n was 0 to 2 and the content of the component of Chemical Formula 4 was 45.9% when n was 0). The yield was 99% (based on a theoretical yield according to the equivalence ratio of the reaction solution). The above-described % is the percentage of the peak area ratio (the ratio of monomer and polymer components) of a gel permeation chromatography (GPC) (Waters: Waters707).

Figure 1B:
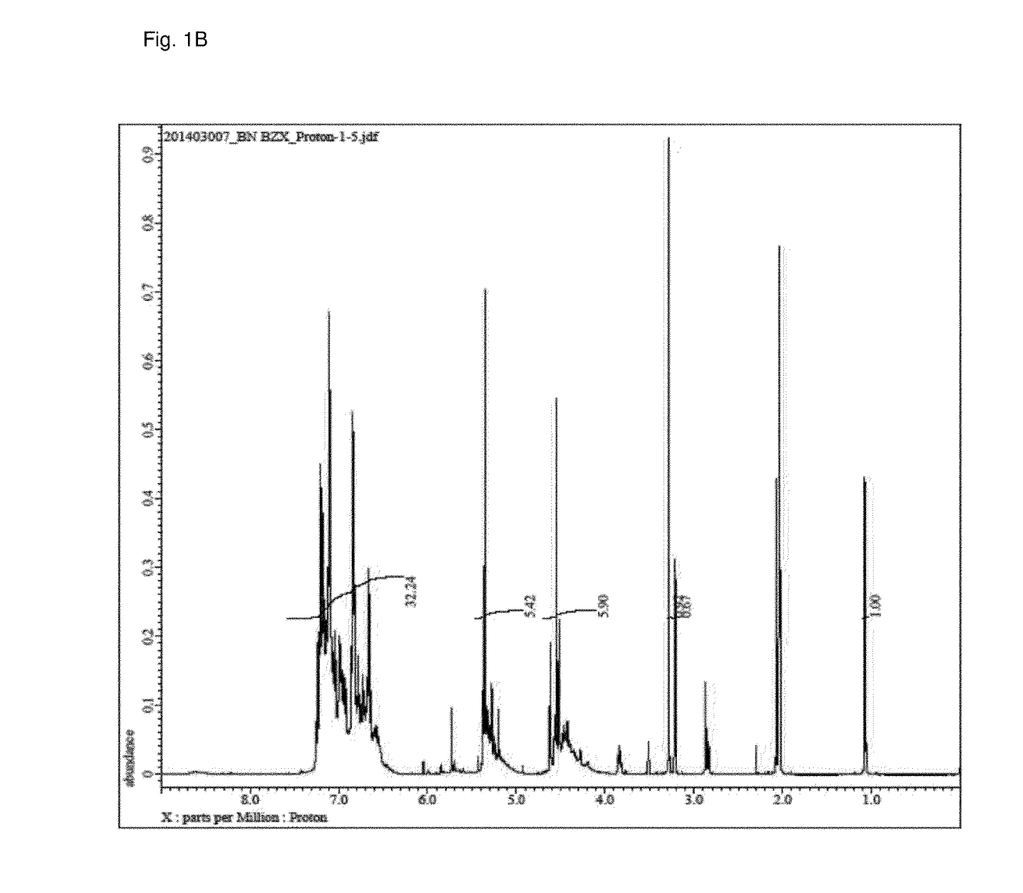
FIG. 1B shows the $^1$H-NMR spectrum of a polybenzoxazime precursor prepared in Example 1 of the present invention.

The structure of the polybenzoxazime precursor thus obtained was confirmed using a nuclear magnetic resonance analysis method ($^1$H-NMR). The result is shown in FIG. 1B. It could be confirmed that an —OH peak was not observed around 8.0 to 9.0 ppm, unlike in FIG. 1A, but that a peak resulting from oxazine was formed around 4.0 to 6.0 ppm.

Figure 1C:
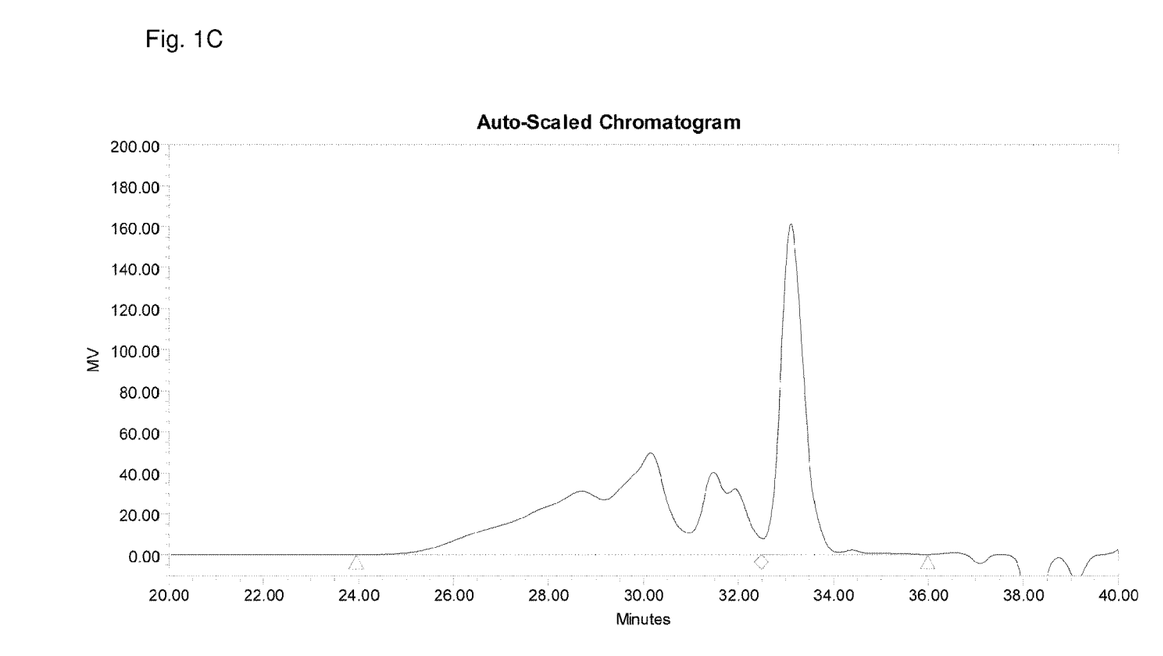
FIG. 1C shows the result of GPC analysis of the polybenzoxazime precursor prepared in Example 1 of the present invention.

Meanwhile, molecular weight data of the polybenzoxazime precursor were analyzed using a GPC (gel permeation chromatograph, Waters: Waters707), and the result is shown in FIG. 1C.

From the result of FIG. 10, it was confirmed that a broad peak indicating a high-molecular-weight material was observed at a retention time of about 30 min. This is considered to result from the generation of the self-hardened material of the compound represented by Chemical Formula 4, that is, the compound represented by Chemical Formula 5.

1-2: Preparation of Hardened Material

The polybenzoxazime precursor obtained in Example 1-1 was added to an aluminum plate having a diameter of 30 mm, and was self-hardened at 220° C. for 2 hours, thus preparing a sheet-type hardened material having a thickness of 1.5 mm.

EXAMPLE 2

2-1: Preparation of Polybenzoxazime Precursor 197.33 g of benzaldehyde and 1250 g of phenol were added at 40° C. and were reacted under a para-toluene sulfonic acid catalyst, which was an acid catalyst, at 130° C. for 4 hours, thus obtaining a phenol novolak resin containing 75.27% of 4,4-(phenylmethylene)diphenol (GPC area %) and 24.73% of the compound represented by Chemical Formula 3, where n was 1 to 2, as the residue.

Next, 500 g (3.5262 mol) of the synthesized phenol novolak resin and 276.1 g of toluene were added to a 3 L three-neck flask subjected to purging using nitrogen. 328.39 g (3.5262 mol) of aniline and 529.46 g (7.0524 mol) of a formaldehyde aqueous solution (40%) were added thereto. After the completion of addition, the temperature of the reaction solution was increased to 100° C. at a heating rate of 1.3° C./min, and the reaction solution was then agitated for 5 hours. Subsequently, the temperature was increased to 130° C. and a solvent was completely removed under a pressure of 10 torr for 60 min, thus preparing 905 g of a polybenzoxazime precursor having a weight average molecular weight of 889 g/mol (the polybenzoxazime precursor included the component represented by Chemical Formula 4 where n was 0 to 2 and the content of the component of Chemical Formula 4 was 34.57% when n was 0). The yield was 99% (based on a theoretical yield according to the equivalence ratio of the reaction solution). The above-described % is the percentage of the peak area ratio (the ratio of monomer and polymer components) of gel permeation chromatography (GPC) (Waters: Waters707).

Figure 2:
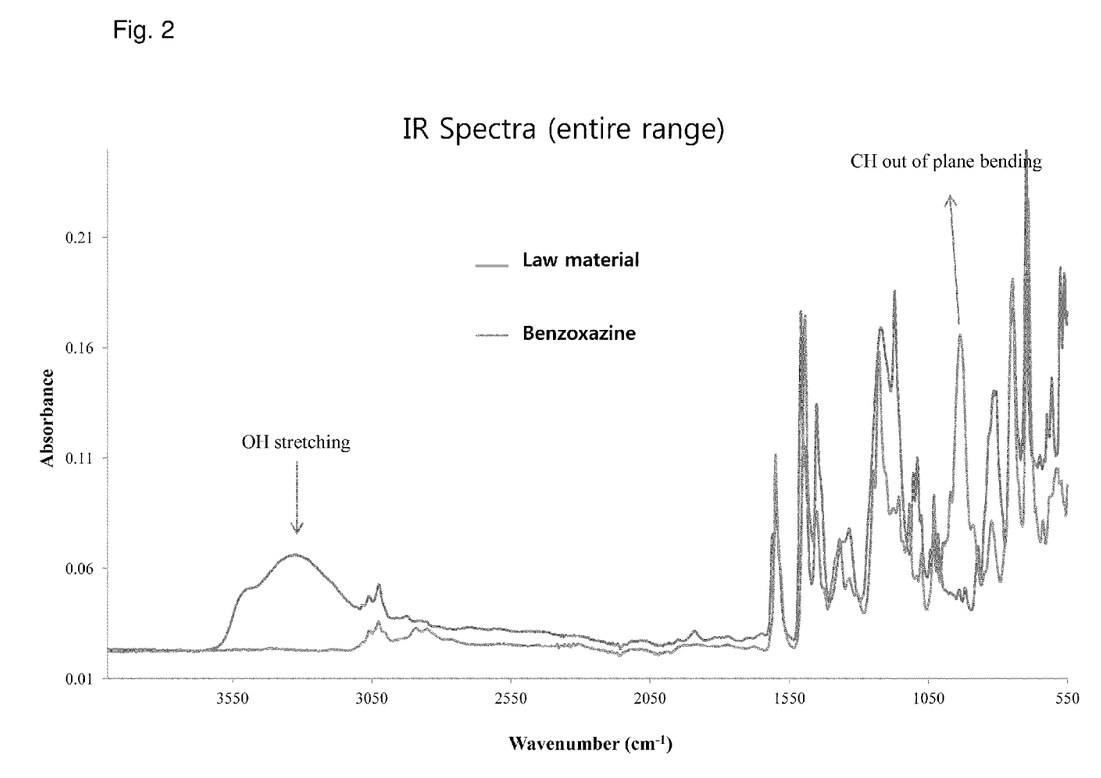
FIG. 2 is a comparative view showing infrared spectroscopy (IR) spectra of the polybenzoxazime precursor prepared in Example 2 of the present invention and a phenol novolak resin, which is a raw material.

The structure of the obtained polybenzoxazime precursor was confirmed using infrared spectroscopy. The result is shown in FIG. 2, and the hydrogen atom peak of an oxazine ring (CH out of plane bending) could be confirmed. A Spectrum 100, manufactured by PerkinElmer, Inc. was used as the infrared spectroscopy equipment.

From FIG. 2, it could be confirmed that an —OH stretching peak resulting from an —OH group was not observed but that the characteristic peak of benzoxazine was observed (926 cm$^{-1}$ (the out-of-plane bending vibration of C—H) and 1234 cm$^{-1}$ (C—O—C asymmetric stretching modes)) in the case of the polybenzoxazime precursor designated by benzoxazine in FIG. 2, compared to the phenol novolak resin of Chemical Formula 3, which was a raw material.

Meanwhile, the molecular weight data of the polybenzoxazime precursor were analyzed using a GPC (gel permeation chromatograph, Waters: Waters707) (not shown). A broad peak indicating a high molecular weight was observed at a retention time of about 30 min. Thereby, it was considered that the self-hardened material of the compound represented by Chemical Formula 4, that is, the compound represented by Chemical Formula 5, was formed.

2-2: Preparation of Hardened Material

The polybenzoxazime precursor obtained in Example 2-1 was added to an aluminum plate having a diameter of 30 mm, and was self-hardened at 1220° C. for 2 hours, thus preparing a sheet-type hardened material having a thickness of 1.5 mm.

COMPARATIVE EXAMPLE 1

1-1: Preparation of Polybenzoxazime Precursor 484.2 g of toluene was added to a 3 L three-neck flask subjected to purging using nitrogen. 652.71 g (2.0 mol) of aniline and 800 g (1 mol) of bisphenol A were added thereto. After the completion of the addition, the temperature of the reaction solution was increased to 100° C. at a heating rate of 1.3° C./min, and the reaction solution was then agitated for 5 hours. Subsequently, the temperature was increased to 120° C., and a solvent was completely removed under pressure of 10 torr for 60 min, thus preparing 1500 g of a polybenzoxazime precursor having a weight average molecular weight of 698 g/mol. The benzoxazine-based compound that was obtained included 54.26% (GPC area %) of a benzoxazine monomer, and a yield was 92% (based on a theoretical yield according to the equivalence ratio of the reaction solution). The above-described % is the percentage of the peak area ratio (the ratio of monomer and polymer components) obtained through gel permeation chromatography (GPC) (Waters: Waters707).

1-2: Preparation of Hardened Material

The polybenzoxazime precursor obtained in Comparative Example 11 was added to an aluminum plate having a diameter of 30 mm, and was self-hardened at 220° C. for 3 hours, thus preparing a sheet-type hardened material having a thickness of 1.5 mm.

COMPARATIVE EXAMPLE 2

2-1: Preparation of Polybenzoxazime Precursor 514.7 g of toluene was added to a 3 L three-neck flask subjected to purging using nitrogen. 744.18 g (2.0 mol) of aniline and 800 g (1 mol) of bisphenol F were added thereto. After the completion of the addition, the temperature of the reaction solution was increased to 100° C. at a heating rate of 1.3° C./min, and the reaction solution was then agitated for 5 hours. Subsequently, the temperature was increased to 120° C., and a solvent was completely removed under pressure of 10 torr for 60 min, thus preparing 945 g of a polybenzoxazime precursor having a weight average molecular weight of 1240 g/mol. The polybenzoxazime precursor that was obtained included 22.58% (GPC area %) of a benzoxazine monomer, and a yield was 93% (based on a theoretical yield according to the equivalence ratio of the reaction solution). The above-described % is the percentage of the peak area ratio (the ratio of monomer and polymer components) of a gel permeation chromatography (GPC) (Waters: Waters707).

2-2: Preparation of Hardened Material

The polybenzoxazime precursor obtained in Comparative Example 2-1 was added to an aluminum plate having a diameter of 30 mm, and was self-hardened at 220° C. for 2 hours, thus preparing a sheet-type hardened material having a thickness of 1.5 mm.

1-2: Preparation of Hardened Material

The polybenzoxazime obtained in Comparative Example 1-1 was added to an aluminum plate having a diameter of 30 mm and was self-hardened at 220° C. for 3 hours, thus preparing a sheet-type hardened material having a thickness of 1.5 mm.

The molecular weights of the polybenzoxazime precursors prepared in Examples 1 and 2 and Comparative Examples 1 and 2 were measured using the following method, and the results are described in the following Table 1.

<Measurement of Molecular Weight>

The weight average molecular weight (Mw) and the number average molecular weight (Mn) of the converted equivalent of polystyrene were obtained via gel permeation chromatography (GPC) (Waters: Waters707). The sample to be measured was dissolved in tetrahydrofuran so that the concentration was 4000 ppm, and the resulting solution was injected in an amount of 100 μl into the GPC. Tetrahydrofuran was used as the mobile phase of the GPC and was added at a flow rate of 1.0 mL/min, and analysis was performed at 35° C. Four columns of Waters HR-05, 1, 2, and 4E were connected in series. As for the detector, RI and PAD detectors were used in measurement at 35° C.

Meanwhile, the glass transition temperature, the thermal decomposition temperature (Td), the flame retardancy, and the permittivity of the hardened materials prepared in Examples 1 and 2 and Comparative Examples 1 and 2 were measured using the following methods, and the results are described in the following Table 1.

<Measurement of Glass Transition Temperature (Tg)>

10 mg of each of the hardened materials prepared in Examples 1 and 2 and Comparative Examples 1 and 2 was measured using a TA Instruments DSC Q2000 as a DSC (differential scanning calorimeter) while being heated from 30° C. to 350° C. at a heating rate of 20° C./min.

<Measurement of Flame Retardancy>

The flame retardancy of the hardened materials prepared in Examples 1 and 2 and Comparative Examples 1 and 2 was evaluated according to a UL-94 method.

<Measurement of Permittivity>

The permittivity (Dk) and the dielectric tangent (Df) of the hardened material were measured using an impedance analyzer (Agilent E4991A 1 MHz to 3 GHz) manufactured by Agilent company under the following conditions.

Measured frequency: 1 GHz
Measured temperature: 25 to 27° C.
Measured humidity: 45 to 55%
Measured sample: thickness 1.5 mm (1.3 to 1.7 mm)

TABLE 1

| Classification | Mn/Mw (g/mol) | Tg (° C.) | Flame retardancy (UL94-V0) | Permittivity (Dk)/dielectric tangent (Df) |
|---|---|---|---|---|
| Example 1 | 514/652 | 203 | V0 | 3.28/0.01 |
| Example 2 | 757/889 | 205 | V0 | 3.22/0.01 |
| Comparative Example 1 | 520/698 | 170.48 | impossible to measure (burns) | 3/0.01 |
| Comparative Example 2 | 571/1240 | 173.7 | V1 | 3.45/0.015 |

As seen from Table 1, the permittivity values of Examples 1 and 2 and Comparative Examples 1 and 2 were similar to each other, but the glass transition temperature and the flame retardancy were higher in Examples 1 and 2 than in Comparative Examples 1 and 2. Accordingly, in Examples 1 and 2, thermal and flame-retardant characteristics were excellent, and in the case of Comparative Example 1, since the hardened material was burnt during the measurement process, the result of measurement could not be obtained.

EXAMPLE 3

3-1: Preparation of Polybenzoxazime Precursor 202.97 g of benzaldehyde and 1200.0 g of phenol were added at 40° C., and were reacted under a para-toluene sulfonic acid catalyst, which was an acid catalyst, at 130° C. for 5 hours, thus obtaining a phenol novolak resin containing 77.14% (GPC area %) of the compound represented by the following Chemical Formula 3, where n was 0, and 22.86% of the compound represented by Chemical Formula 3, where n was 1 to 2, as the residue.

Next, 500 g (1.7665 mol) of the synthesized phenol novolak resin and 609.3 g of toluene were added to a 3 L three-neck flask subjected to purging using nitrogen. 201.70 g (3.5331 mol) of allylamine and 530.49 g (7.0661 mol) of a formaldehyde aqueous solution (40%) were added thereto. After the completion of addition, the temperature of the reaction solution was increased to 100° C. at a heating rate of 1.3° C./min, and the reaction solution was then agitated for 5 hours. Subsequently, the temperature was increased to 120° C., and a solvent was completely removed under pressure of 10 torr for 60 min, thus preparing 787 g of a polybenzoxazime precursor having a weight average molecular weight of 1420 g/mol (the polybenzoxazime precursor included the component represented by Chemical Formula 6 where n was 0 to 2 and the content of the component of Chemical Formula 6 was 30.7% when n was 0). A yield was 99% (based on a theoretical yield according to the equivalence ratio of the reaction solution). The above-described % is the percentage of the peak area ratio (the ratio of monomer and polymer components) obtained through gel permeation chromatography (GPC) (Waters: Waters707).

Figure 3:
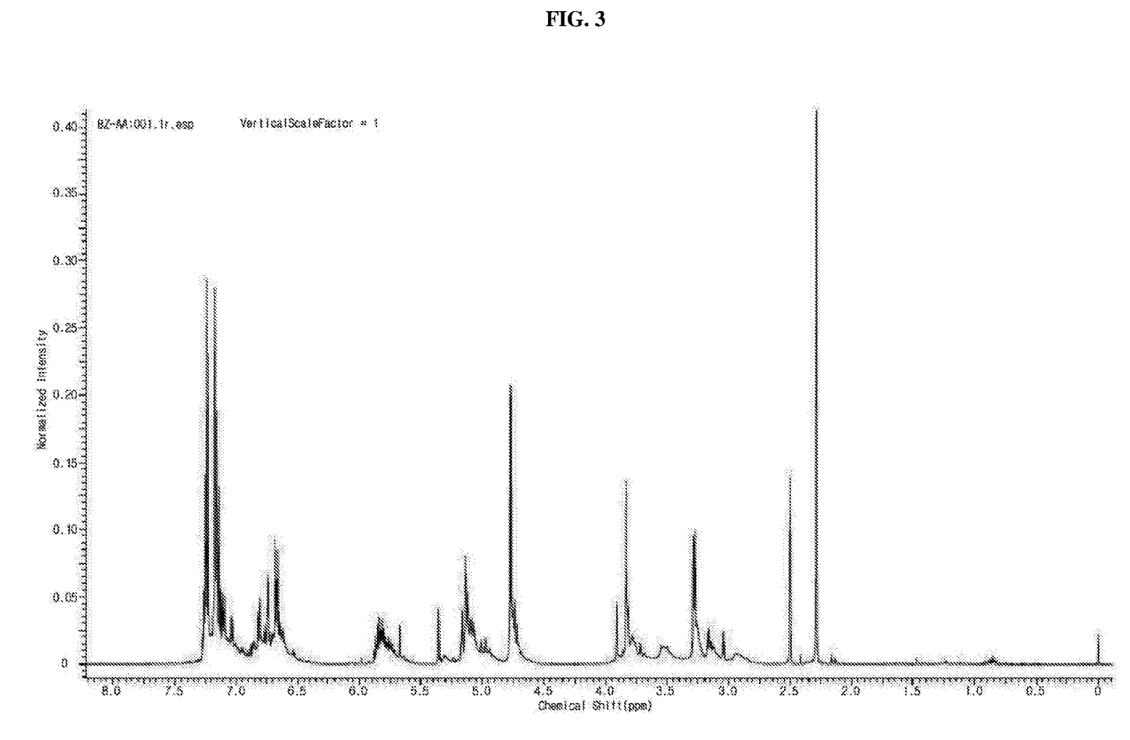
FIG. 3 shows the $^1$H-NMR spectrum of the polybenzoxazime precursor prepared in Example 3 of the present invention.

The structure of the obtained benzoxazine was confirmed using a nuclear magnetic resonance analysis method ($^1$H-NMR). The result is shown in FIG. 3. It could be confirmed that an -OH peak was not observed around 8.0 to 9.0 ppm but that a peak resulting from oxazine was formed around 4.0 to 6.0 ppm, compared to the NMR data of the phenol novolak resin of FIG. 1A. An Avance 500, manufactured by Bruker Co., Ltd. was used as NMR equipment during NMR analysis.

Meanwhile, molecular weight data of the polybenzoxazime precursor were analyzed using a GPC (gel permeation chromatograph, Waters: Waters707) (not shown). A broad peak indicating a high molecular weight was observed at a retention time of about 30 min. Thereby, it was considered that the self-hardened material of the compound represented by Chemical Formula 5, that is, the compound represented by Chemical Formula 7, was formed.

3-2: Preparation of Hardened Material

The polybenzoxazime precursor obtained in Example 3-1 was added to an aluminum plate having a diameter of 30 mm, and was self-hardened at 220° C. for 2 hours, thus preparing a sheet-type hardened material having a thickness of 1.5 mm.

EXAMPLE 4

4-1: Preparation of Polybenzoxazime Precursor 197.33 g of benzaldehyde and 1250 g of phenol were added at 40° C., and were reacted under a para-toluene sulfonic acid catalyst, which was an acid catalyst, at 130° C. for 4 hours, thus obtaining a phenol novolak resin containing 75.27% (GPC area %) of the compound represented by Chemical Formula 3 where n was 0 and 24.73% of the compound represented by Chemical Formula 3 where n was 1 to 2 as the residue.

Next, 500 g (1.7665 mol) of the synthesized phenol novolak resin and 609.3 g of toluene were added to a 3 L three-neck flask subjected to purging using nitrogen. 201.70 g (3.5331 mol) of allylamine and 530.49 g (7.0661 mol) of a formaldehyde aqueous solution (40%) were added thereto. After the completion of addition, the temperature of the reaction solution was increased to 100° C. at a heating rate of 1.3° C./min, and the reaction solution was then agitated for 5 hours. Subsequently, the temperature was increased to 120° C., and a solvent was completely removed under pressure of 10 torr for 60 min, thus preparing 781 g of a polybenzoxazime precursor having a weight average molecular weight of 1264 g/mol (the polybenzoxazime precursor included the component represented by Chemical Formula 6 where n was 0 to 2 and the content of the component of Chemical Formula 6 was 32.7% when n was 0). The yield was 99% (based on a theoretical yield according to the equivalence ratio of the reaction solution). The above-described % is the percentage of the peak area ratio (the ratio of monomer and polymer components) obtained through gel permeation chromatography (GPC) (Waters: Waters707).

Figure 4:
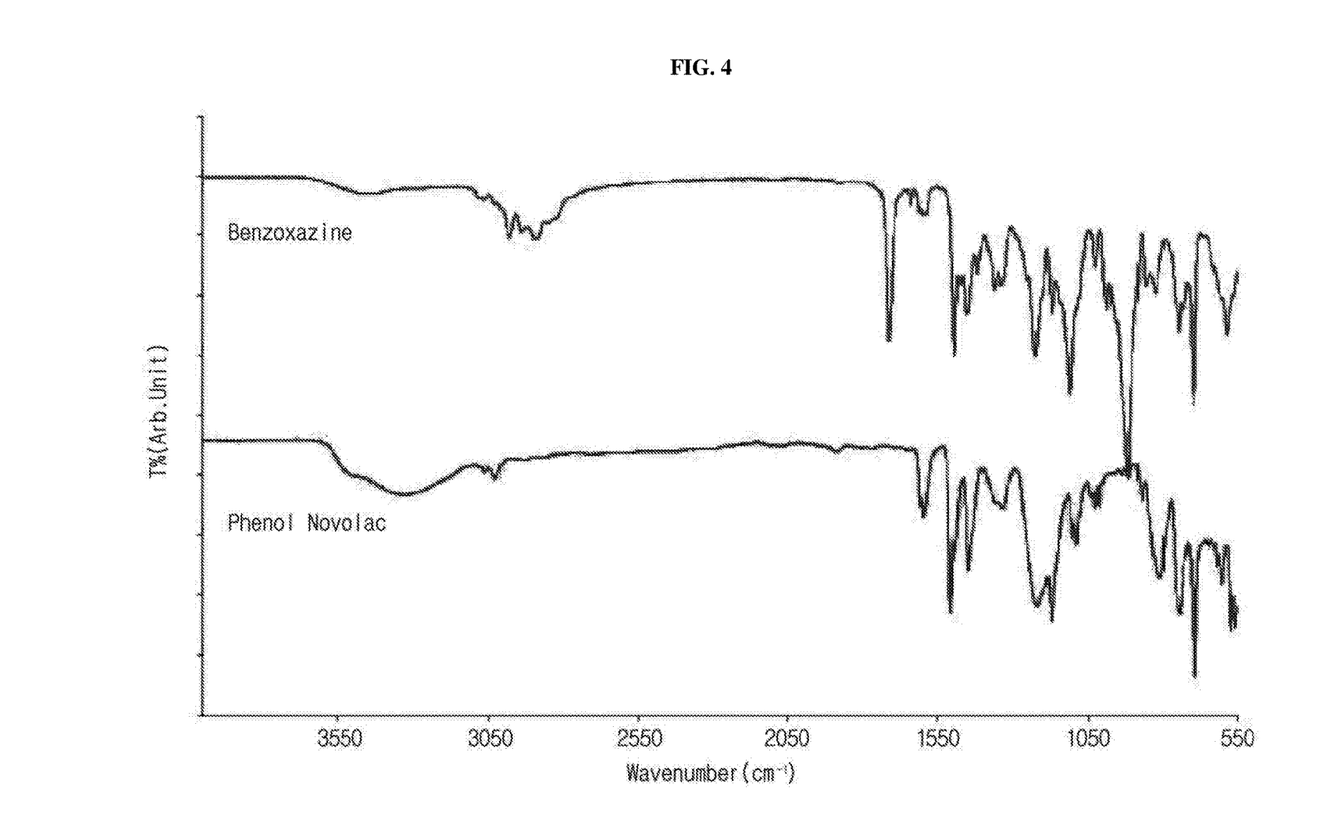
FIG. 4 is a comparative view showing infrared spectroscopy (IR) spectra of the polybenzoxazime precursor prepared in Example 4 of the present invention and a phenol novolak resin, which is a raw material.

The structure of the obtained benzoxazine monomer was confirmed using infrared spectroscopy. The result is shown in FIG. 4. In FIG. 4, phenol novolac denotes the phenol novolak resin represented by Chemical Formula 3 and benzoxazine denotes the obtained polybenzoxazime precursor. In the case of benzoxazine, an —OH stretching peak resulting from an —OH group was not observed, but the characteristic peak of benzoxazine was observed (926 cm$^{-1}$ (the out-of-plane bending vibration of C-H) and 1234 cm$^{-1}$ (C—O—C asymmetric stretching modes)). A Spectrum 100 manufactured by PerkinElmer, Inc. was used as the infrared spectroscopy equipment.

Meanwhile, molecular weight data of the polybenzoxazime precursor were analyzed using a GPC (gel permeation chromatograph, Waters: Waters707) (not shown). A broad peak indicating a high molecular weight was observed at a retention time of about 30 min. Thereby, it was considered that the self-hardened material of the compound represented by Chemical Formula 5, that is, the compound represented by Chemical Formula 7, was formed.

4-2: Preparation of Hardened Material

The polybenzoxazime obtained in Example 4-1 was added to an aluminum plate having a diameter of 30 mm, and was self-hardened at 1220° C. for 2 hours, thus preparing a sheet-type hardened material having a thickness of 1.5 mm.

The molecular weights of the polybenzoxazime precursors of Examples 3 and 4 were measured using the above-described method, and the results are described in the following Table 2 for comparison with the results of Comparative Examples 1 and 2.

Meanwhile, the flame retardancy and the permittivity of the hardened materials prepared in Examples 3 and 4 were measured using the above-described method, and the results are described in the following Table 2 for comparison with the results of Comparative Examples 1 and 2.

However, the glass transition temperature was measured using the following method, and the result is described in the following Table 2.

<Measurement of Glass Transition Temperature (Tg)>

Since it was difficult to confirm the Tg of the hardened materials prepared in Examples 3 and 4 using the DSC due to the structure thereof, Tg was measured using DMA (dynamic mechanical analysis).

Therefore, the hardened materials prepared in Examples 3 and 4 and Comparative Examples 1 and 2 were measured in terms of Tg using a TA Instruments DMA Q800 while being heated from 30° C. to 350° C. at a heating rate of 3° C./min.

TABLE 2

| Classification | Mn/Mw (g/mol) | Tg (° C.) | Td 5 (° C.) | Permittivity (Dk) | Dielectric tangent (Df) |
|---|---|---|---|---|---|
| Example 3 | 668/1420 | 302 | 351.7 | 2.95 | 0.0020 |
| Example 4 | 638/1264 | 298 | 349.4 | 2.98 | 0.0025 |
| Comparative Example 1 | 520/698 | 198.7 | 314.6 | 3.00 | 0.0100 |
| Comparative Example 2 | 571/1240 | 195.9 | 318.2 | 3.45 | 0.0150 |

As seen from Table 2, the Tg and Td values were higher in Examples 3 and 4 than in Comparative Examples 1 and 2. Accordingly, Examples 3 and 4 exhibited excellent thermal characteristics. Particularly, in Examples 3 and 4, the permittivity (Dk) and the dielectric tangent (Df) were low when measured, and accordingly the electrical characteristics were excellent.

All simple modifications or variations of the present invention may be easily performed by those skilled in the art, and may be incorporated in the scope of the present invention. Invention as disclosed in the accompanying claims.

The invention claimed is:

1. A polybenzoxazine precursor comprising:
a benzoxazine compound of the following Chemical Formula 1:

Chemical Formula 1 wherein n is an integer of 0 to 2, and
$R_1$ is wherein the benzoxazine compound is comprised of at least 20% of the compound of Chemical Formula 1 of which n is 0 and remainder of the compound of Chemical Formula 1 of which n is 1 to 2.

2. The polybenzoxazine precursor of claim 1, wherein the precursor includes a self-hardened material obtained by opening an oxazine ring of the benzoxazine compound represented by Chemical Formula 1 to perform polymerization.

3. The polybenzoxazine precursor of claim 2, wherein the self-hardened material of the benzoxazine compound includes a compound represented by the following Chemical Formula 2:

Chemical Formula 2 wherein R is

$R_1$ is n is an integer of 0 to 2, and n2 is an integer of 1 to 5.

4. The polybenzoxazine precursor of claim 1, wherein a weight average molecular weight is 500 to 5000 g/mol.

5. A method of preparing a polybenzoxazine precursor comprising polybenzoxazine compound of the following Chemical Formula 1:

Chemical Formula 1 wherein n is an integer of 0 to 2, and
$R_1$ is wherein the benzoxazine compound is comprised of at least 20% of the compound of Chemical Formula 1 of which n is 0 and remainder of the compound of Chemical Formula 1 of which n is 1 to 2, comprising the steps of:

(1) obtaining a phenol novolak resin by reacting a phenol-based compound with an aldehyde compound in the presence of an acid catalyst; and (2) reacting the obtained phenol novolak resin with an aldehyde compound and an amine compound incluidng allylamine or aniline.

6. The method of claim 5, wherein the phenol novolak resin is represented by Chemical Formula 3, wherein a content of the phenol novolak resin represented by Chemical Formula 3that n is 0 is 65% or more Chemical Formula 3 wherein n is an integer of 0 to 2.

7. The method of claim 5, wherein the aldehyde compound is used in a content of 0.05 to 0.3 mol based on 1 mol of the phenol-based compound in the step (1), and the amine compound is used in a content of 1 to 3 mol and the aldehyde compound is used in a content of 1 to 5 mol based on 1mol of the phenol novolak resin in the step (2).

8. A hardened material of the polybenzoxazine precursor of claim 1.

9. The hardened material of claim 8, wherein the hardened material includes a self-hardened material of the polybenzoxazine precursor including a benzoxazine compound represented by Chemical Formula 1 where $R_1$ is and has a glass transition temperature of 190° C. or higher.

10. The hardened material of claim 8, wherein the hardened material includes a self-hardened material of the polybenzoxazine precursor including a benzoxazine compound represented by Chemical Formula 1 where $R_1$ is and has a glass transition temperature of 250° C. or higher.

11. A hardened material of the polybenzoxazine precursor of claim 2.

12. The hardened material of claim 11, wherein the hardened material includes a self-hardened material of the polybenzoxazine precursor including a benzoxazine compound represented by Chemical Formula 1 where $R_1$ is and has a glass transition temperature of 190° C. or higher.

13. The hardened material of claim 11, wherein the hardened material includes a self-hardened material of the polybenzoxazine precursor including a benzoxazine compound represented by Chemical Formula 1 where $R_1$ is and has a glass transition temperature of 250° C. or higher.

14. A hardened material of the polybenzoxazine precursor of claim 3.

15. The hardened material of claim 14, wherein the hardened material includes a self-hardened material of the polybenzoxazine precursor including a benzoxazine compound represented by Chemical Formula 1 where $R_1$ is and has a glass transition temperature of 190° C. or higher.

16. The hardened material of claim 14, wherein the hardened material includes a self-hardened material of the polybenzoxazine precursor including a benzoxazine compound represented by Chemical Formula 1 where $R_1$ is and has a glass transition temperature of 250° C. or higher.

17. A hardened material of the polybenzoxazine precursor of claim 4.

18. The hardened material of claim 17, wherein the hardened material includes a self-hardened material of the polybenzoxazine precursor including a benzoxazine compound represented by Chemical Formula 1 where $R_1$ is and has a glass transition temperature of 190° C. or higher.

19. The hardened material of claim 17, wherein the hardened material includes a self-hardened material of the polybenzoxazine precursor including a benzoxazine compound represented by Chemical Formula 1 where $R_1$ is and has a glass transition temperature of 250° C. or higher.

* * * * *